(12) United States Patent
Aieta et al.

(10) Patent No.: US 10,458,846 B2
(45) Date of Patent: Oct. 29, 2019

(54) SPECTRAL MICROSCOPE

(71) Applicant: Hewlett-Packard Development Company, L.P., Houston, TX (US)

(72) Inventors: Francesco Aieta, San Francisco, CA (US); Charles M. Santori, Palo Alto, CA (US); Anita Rogacs, San Diego, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 15/748,611

(22) PCT Filed: Aug. 31, 2015

(86) PCT No.: PCT/US2015/047774
§ 371 (c)(1),
(2) Date: Jan. 29, 2018

(87) PCT Pub. No.: WO2017/039620
PCT Pub. Date: Mar. 9, 2017

(65) Prior Publication Data
US 2019/0003892 A1   Jan. 3, 2019

(51) Int. Cl.
*G01J 3/30*      (2006.01)
*G01N 21/64*  (2006.01)
(Continued)

(52) U.S. Cl.
CPC ............... *G01J 3/30* (2013.01); *G01J 3/0208* (2013.01); *G01J 3/0248* (2013.01);
(Continued)

(58) Field of Classification Search
CPC ........ G01J 3/02; G01J 3/30; G01J 3/44; G01J 1/42; G01N 21/64; G01N 15/14; G02B 21/16; G02B 5/18; G02B 6/124
See application file for complete search history.

(56) References Cited

U.S. PATENT DOCUMENTS 7,221,453 B2   5/2007   Sharpe et al.
7,441,703 B2  10/2008   Moon et al.
(Continued)

FOREIGN PATENT DOCUMENTS

WO   WO-2014031900 A1   2/2014

OTHER PUBLICATIONS

International Search Report and Written Opinion dated Apr. 29, 2016, PCT Patent Application No. PCT/US2015/047774, filed Aug. 31, 2015, Korean Intellectual Property Office.
(Continued)

*Primary Examiner* — Abdullahi Nur
(74) *Attorney, Agent, or Firm* — Brooks Cameron & Huebsch PLLC

(57) ABSTRACT

In one implementation, a spectral microscope may comprise a substrate with a planar lens, the planar lens including a phase profile including an axial focus and an oblique focus, a light source to excite a signal of a particle among a plurality of particles, and a detector to receive light generated from the light source from the axial focus of the planar lens and a spectral color component of the excited signal of the particle from the oblique focus of the planar lens.

20 Claims, 4 Drawing Sheets

(51) Int. Cl.
| | |
|---|---|
| G01N 15/14 | (2006.01) |
| G01J 3/02 | (2006.01) |
| G01J 3/28 | (2006.01) |
| G01J 3/44 | (2006.01) |
| G02B 21/00 | (2006.01) |
| G02B 21/16 | (2006.01) |
| G01N 15/00 | (2006.01) |
| G01N 21/65 | (2006.01) |
| G01N 15/10 | (2006.01) |

(52) U.S. Cl.
CPC ........... *G01J 3/0256* (2013.01); *G01J 3/2803* (2013.01); *G01J 3/4406* (2013.01); *G01N 15/1434* (2013.01); *G01N 21/6458* (2013.01); *G02B 21/0008* (2013.01); *G02B 21/0096* (2013.01); *G02B 21/16* (2013.01); *G01N 15/147* (2013.01); *G01N 21/658* (2013.01); *G01N 2015/0053* (2013.01); *G01N 2015/1006* (2013.01); *G01N 2015/149* (2013.01); *G01N 2021/6421* (2013.01)

(56) References Cited

U.S. PATENT DOCUMENTS

| | | |
|---|---|---|
| 8,454,512 B2 | 6/2013 | Wang et al. |
| 2007/0041013 A1* | 2/2007 | Fritz ................ G01N 15/1463 356/338 |
| 2008/0002180 A1 | 1/2008 | Gigioli et al. |
| 2013/0083315 A1 | 4/2013 | Lo et al. |
| 2014/0093949 A1 | 4/2014 | Norton et al. |
| 2014/0315288 A1 | 10/2014 | Miyamura et al. |
| 2014/0339445 A1* | 11/2014 | Sharpe ............ G01N 15/1459 250/574 |

OTHER PUBLICATIONS

Petryayeva, E., et al., "Quantum Dots in Bioanalysis: a Review of Applications Across Various Platforms for Fluorescence Spectroscopy and Imaging", Dec. 18, 2012, Applied Spectroscopy, vol. 67, No. 3, pp. 215-252. http://www.opticsinfobase.org/view_article.cfm?gotourl=http%3A%2F%2Fwww%2Eopticsinfobase%2Eorg%2FDirectPDFAccess%2F204C8075-D51D-906B-7E2FC6491EDC3078_249641%2Fas-67-3-215%2Epdf%3Fda%3D1%26id%3D249641%26seq%3D0%26mobile%3Dno&org.

Schonbrun, E., "Diffractive Optofluidic Imaging Flow Cytometry", May 6-11, 2012, Optical Society of America, CLEO Technical Digest, 2 pages. http://ieeexplore.ieee.org/xpl/articleDetails.jsp?tp=&arnumber=6325426&queryText%3Ddiffractive+optics+cell+imaging+flow+cyrometry.

* cited by examiner

SPECTRAL MICROSCOPE

CLAIM FOR PRIORITY

The present application is a national stage filing under 35 U.S.C. § 371 of PCT application number PCT/US2015/047774, having an international filing date of Aug. 31, 2015, the disclosure of which is hereby incorporated by reference in its entirety.

BACKGROUND

Spectral analysis of fluorescence signals is a common tool used in many different fields of life science. One example of spectral analysis using a spectral microscope is flow cytometry, which may be used for detection and analysis of particles in immunology, molecular biology, and/or cancer detection, among other fields in the life sciences. Spectral analysis in a flow cytometer may provide multiple physical and chemical characteristics of particles.

DETAILED DESCRIPTION

A number of devices and methods for a spectral microscope are described herein. One example of a spectral microscope may be a flow cytometer. A conventional flow cytometer may require the use of combinations of optical components to provide spectral analysis functionalities. For example, a conventional flow cytometer may require optical components such as special gratings and/or prisms with complicated and/or delicate alignment configurations. Additionally, conventional flow cytometers may be large instruments that may be expensive. Size, cost, and complicated and/or delicate alignments of optical components may render conventional flow cytometers unfit for certain functions, such as for point-of-care healthcare applications.

As used herein, a spectral microscope may refer to a device that may provide for imaging as well as spectral detection without the need for complex and delicate optical component alignments. That is, a spectral microscope may comprise a substrate with a planar lens, the planar lens including a phase profile including an axial focus and an oblique focus, a light source to excite a signal of a particle among a plurality of particles, and a detector to receive light generated from the light source from the axial focus of the planar lens and a spectral color component of the excited signal of the particle from the oblique focus of the planar lens.

Figure 1:
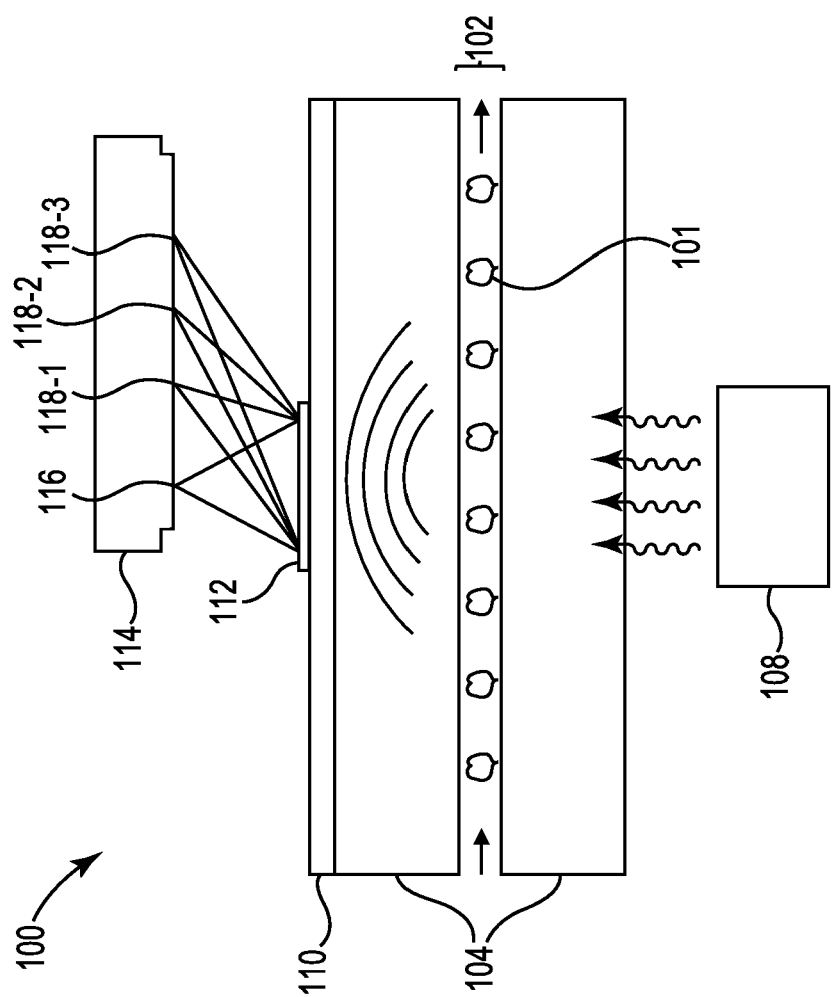
FIG. 1 illustrates a diagram of an example of a spectral microscope consistent with the disclosure.

FIG. 1 illustrates a diagram of an example of a spectral microscope 100 consistent with the disclosure. The spectral microscope 100 may include a transparent chip 104, a channel 102, a particle 101, a substrate 110, a planar diffractive lens 112, a light source 108, and a detector 114. Detector 114 may include an axial position 116 and oblique position 118-1, 118-2, 118-3.

As used herein, a spectral microscope may be a device for particle counting, imaging, sorting and/or detection by passing a fluid comprising particles (e.g., particle 101) by a detection apparatus. As used herein, a particle may be a minute quantity of matter including a fluorescent chemical compound. For example, a particle to be counted, imaged, sorted, and/or detected may range in size from 0.6 micrometers ($\mu$m) to 20.0 $\mu$m, although embodiments of the disclosure are not so limited.

Although spectral microscope 100 is described as a device for particle counting, imaging, sorting, and/or detection, examples of the disclosure are not so limited. For example, spectral microscope 100 may perform other functions related to particles. Additionally, spectral microscope 100 may perform other functions not related to particles involving fluids. For example, spectral microscope 100 may be used for imaging surface-enhanced Raman Spectroscopy substrates, counting cells in a counting chamber, and/or particle counting/analysis in air (e.g., microarrays, fixed cells on slides, etc.), among other functions.

Spectral microscope 100 may include a channel 102 located in a transparent chip 104, wherein the channel 102 may include a plurality of particles (e.g., particle 101). Particle 101 may be a particle among a number of particles suspended in a fluid. For example, particle 101 may be a fluorescent stained red or white blood cell, protein, and/or nucleic acid, among other types of particles suspended in a fluid. Channel 102 may be a microfluidic channel located in transparent chip 104.

Although particle 101 is described as being suspended in a fluid, embodiments of the disclosure are not so limited. For example, particle 101 may be a particle that is not suspended in a fluid.

Transparent chip 104 may be a transparent material to allow light from a light source (e.g., light source 108) to propagate through transparent chip 104, as will be further described herein. For example, transparent chip 104 may be fused silica. As another example, transparent chip 104 may be fused quartz.

Although transparent chip 104 is described as being a transparent material such as fused silica or fused quartz, examples of the disclosure are not so limited. For example, transparent chip 104 may be a type of glass, a transparent polymer, or any other type of transparent material to allow light from light source 108 to propagate through transparent chip 104.

As shown in FIG. 1, spectral microscope 100 may include a substrate 110 with a planar diffractive lens 112. Planar diffractive lens 112 may include a phase profile including an axial focus and an oblique focus. Planar diffractive lens 112 may be a high numerical aperture diffractive lens with two foci (e.g., axial focus and oblique focus). For example, the numerical aperture of planar diffractive lens 112 may be between 0.2 and 0.6, although examples of the disclosure are not so limited. As an additional example, the numerical aperture of planar diffractive lens 112 may be 0.45. The axial focus of planar diffractive lens 112 may be used for imaging and the oblique focus of planar diffractive lens 112 may be used for spectral detection, as will be further described herein.

The phase profile of planar diffractive lens 112 may include an axial phase profile. The axial phase profile of planar diffractive lens 112 may cause light to be focused in an axial manner, which may be referred to as the axial focus of planar diffractive lens 112. For example, light at a specific wavelength may be focused by the axial phase profile in an axial manner at a position on a focal plane of a detector (e.g., axial position 116 on detector 108, as will be further described herein). As used herein, the focal plane of a detector (e.g., detector 108, as will be further described herein) may be a plane that is perpendicular to the axis of planar diffractive lens 112 and passes through a focal point of planar diffractive lens 112.

The phase profile of planar diffractive lens 112 may include an oblique phase profile. The oblique phase profile of planar diffractive lens 112 may cause light to be focused in an oblique manner, which may be referred to as the oblique focus of planar diffractive lens 112. For example, light at various wavelengths may be focused by the oblique phase profile in an oblique manner at various positions on a focal plane of a detector (e.g., oblique positions 118-1, 118-2, 118-3 on detector 108, as will be further described herein).

In some examples, planar diffractive lens 112 may be located on substrate 110. For example, planar diffractive lens 112 may be a lens patterned on substrate 110. Planar diffractive lens 112 may be patterned on substrate 110 by lithography. As used herein, lithography may be a process used in microfabrication or nanofabrication to shape and/or alter deposited materials to form a pattern on a wafer (e.g., substrate 110). The wafer may be coated with a chemical such as a photoresist or electron beam (e-beam) resist, and the wafer then exposed to short wavelength light via a mask or to a beam of electrons. The exposed regions may be washed away by a solution. As another example, nanoimprint lithography may be used to pattern planar diffractive lens 112 on substrate 110. As used herein, nanoimprint lithography may be a process by which patterns are created by mechanical deformation of an imprint resist.

Patterning planar diffractive lens 112 on substrate 110 may include patterning an axial phase profile and an oblique phase profile on substrate 110. For example, the phase profile of planar diffractive lens 112 may include the axial phase profile and the oblique phase profile as a binary approximation of the combination of the axial phase profile and the oblique phase profile. The axial phase profile and the oblique phase profile may be patterned on substrate 110 by a single step of lithography. That is, the phase profile may be a single pattern approximation of an axial phase profile and an oblique phase profile on substrate 110.

The phase profile of planar diffractive lens 112 may be defined by combining the axial phase profile and the oblique phase profile. For example, a sinusoidal grating can be determined for the axial phase profile and the oblique phase profile, and adding the axial phase profile and the oblique phase profile results in the phase profile of planar diffractive lens 112.

In some examples, the phase profile of planar diffractive lens 112 may be defined by iterative numerical optimization. For example, phases in the focal plane can be used as free parameters, and the target function may be defined as the maximum focused intensities at the desired locations (e.g., axial and/or oblique) for the wavelengths of interest.

In some examples, planar diffractive lens 112 may be divided into discrete spatial zones. For example, one spatial zone can include the axial phase profile and the other spatial zone can include the oblique phase profile. The phase profile of planar diffractive lens 112 is then wrapped and approximated by a discrete number of phase levels corresponding to discrete etch depths in substrate 110.

Substrate 110 with planar diffractive lens 112 may be located adjacent to transparent chip 104. For example, substrate 110 may be located such that light from light source 108 propagates through transparent chip 104, through substrate 110, and finally through planar diffractive lens 112, as will be further described herein.

Substrate 110 may be a transparent material to allow light from a light source (e.g., light source 108) to propagate through substrate 110. Substrate 110 may be chosen according to the wavelength of operation of light source 108, as will be further described herein. For example, substrate 110 may be glass, a graded fused silica, quartz, or calcium fluoride. Glass, graded fused silica, quartz, and calcium fluoride may allow for propagation of the light generated by light source 108 through substrate 110 while reducing material losses to the light, as these materials more easily allow light propagation in the ultra-violet (UV) and near infrared spectra.

Although substrate 110 is described as being glass, graded fused silica, quartz, or calcium fluoride, examples of the disclosure are not so limited. For example, substrate 110 may be any material to allow for propagation of light generated by light source 108 without significant material losses to the light as the light propagates through substrate 110.

Although not shown in FIG. 1, in some examples planar diffractive lens 112 may be located directly on transparent chip 104. For example, planar diffractive lens 112 may be a lens patterned on transparent chip 104. Planar diffractive lens 112 may be patterned on transparent chip 104 by lithography. Planar diffractive lens 112 may alternatively be a layer of e-beam, photo, or imprint resist spun on the substrate and patterned.

Although not shown in FIG. 1, in some examples detector 114 may be located adjacent to substrate 110, and planar diffractive lens 112 may be located between and adjacent to substrate 110 and transparent chip 104. For example, planar diffractive lens 112 may be adjacent to transparent chip 104 and substrate 110 may act as a window for detector 114.

Patterning planar diffractive lens 112 on transparent chip 104 may include patterning an axial phase profile and an oblique phase profile on transparent chip 104 by lithography. For example, the phase profile of planar diffractive lens 112 may include the axial phase profile and the oblique phase profile as a binary approximation of the combination of the axial phase profile and the oblique phase profile. The axial phase profile and the oblique phase profile may be patterned on transparent chip 104 by a single step of lithography. That is, the phase profile may be a single pattern approximation of an axial phase profile and an oblique phase profile on substrate 110.

Spectral microscope 100 may include light source 108 to excite a signal of particle 101 among the plurality of particles. As used herein, a signal may be a fluorescent signal (e.g., light emitted) from a particle (e.g., particle 101) as a result of the particle absorbing (e.g., from light source 108) light (e.g., electromagnetic radiation) from a light source (e.g., light source 108, as will be further described herein) and becoming excited.

Light source 108 may be a light emitting diode (LED). As used herein, an LED may be a semiconductor light source which emits light when activated. For example, light source 108 may be an LED that emits light that is directed towards particle 101 in channel 102, as will be further described herein. The LED may operate across the visible range (e.g., 400-700 nm), ultra-violet (UV) range (e.g., 10-400 nm), and/or infrared range (e.g., 1 mm-700 nm).

Light source 108 may be a laser. As used herein, a laser may be a device that emits light through optical amplification based on emission of electromagnetic radiation. For example, light source 108 may be a laser that emits light that is directed towards particle 101 in channel 102, as will be further described herein. The laser may operate across the visible range (e.g., 400-700 nm), ultra-violet (UV) range (e.g., 10-400 nm), and/or infrared range (e.g., 1 mm-700 nm).

Light source 108 may have a light intensity strong enough to produce fluorescent excitation of the fluorescent signal of particle 101 to be detected by a detector (e.g., detector 114). For example, light source 108 may be an LED with a power of 100 Milliwatts (mW). As another example, light source 108 may be a laser with a power of 1 mW. As used herein, fluorescent excitation may refer to a particle receiving light at a particular wavelength and subsequently emitting light at another wavelength.

Although light source 108 is described as an LED with a power of 100 mW or a laser with a power of 1 mW, examples of the disclosure are not so limited. For example, light source 108 may be an LED or a laser with a higher or lower power. Although not shown in FIG. 1 for clarity and so as not to obscure embodiments of the disclosure, light generated from light source 108 may be focused on channel 102 by an external lens.

The light intensity of light source 108 may be selected depending on a number of factors. For example, a type of fluid in channel 102, a type of particle 101, the efficiency of planar diffractive lens 112, the type of material of transparent chip 104, and substrate 110, and the sensitivity of detector 114 may all influence the light intensity of light source 108. For example, the light intensity of light source 108 may be 1 mW for an LED light source when particle 101 is a red blood cell with a selectively attached fluorophore, and may be 2 mW when particle 101 is a red blood cell with a different selectively attached fluorophore, although examples of the disclosure are not so limited. As used herein, a fluorophore may be a fluorescent chemical compound that can re-emit light upon light excitation, wherein a fluorophore may be attached to certain particles to function as a marker.

Spectral microscope 100 may include a detector 114. Detector 114 may receive light generated from light source 108 from the axial focus of planar diffractive lens 112, and a spectral color component of the fluorescent signal of particle 101 from the oblique focus of planar diffractive lens 112.

Detector 114 may receive light generated from light source 108 from the axial focus of planar diffractive lens 112 at axial position 116. For example, the axial phase profile of planar diffractive lens 112 may cause light from light source 108 to be focused in an axial manner to axial position 116 on the focal plane of detector 114. Light received at axial position 116 of detector 114 may be used to image particle 101, as will be further described herein.

Detector 114 may receive a spectral color component of the fluorescent signal of particle 101 from the oblique focus of planar diffractive lens 112. For example, the oblique phase profile of planar diffractive lens 112 may cause light from light source 108 to be focused in an oblique manner to various oblique positions 118-1, 118-2, 118-3 on the focal plane of detector 114. Although not shown in FIG. 1, a color filter may be placed between planar diffractive lens 112 and the portion of detector 114 that receives the spectral color component of particle 101. The color filter can be selected to block light from light source 108 to improve detection of the fluorescent signal of particle 101.

Light received at oblique positions 118-1, 118-2, 118-3 of detector 114 may be used to detect the wavelength of the fluorescent signal of particle 101. Detector 114 may determine the wavelength of the fluorescent signal of particle 101 by determining which oblique position 118-1, 118-2, 118-3 the spectral color component of the light from light source 108 is received at.

Oblique positions 118-1, 118-2, 118-3 of detector 114 may correspond to different spectral color components. For example, oblique position 118-1 may correspond to a first spectral color component, oblique position 118-2 may correspond to a second spectral color component, and oblique position 118-3 may correspond to a third spectral color component.

The spectral color component of the oblique focus may correspond to a wavelength of the excited (e.g., fluorescent) signal of particle 101. For example, the first spectral color component corresponding to oblique position 118-1 may correspond to a wavelength corresponding to the fluorescent signal of particle 101. That is, particle 101 may have a fluorescent signal with a first spectral color component that corresponds to a certain wavelength, where the first spectral color component is received at detector 114 at oblique position 118-1.

As another example, the second spectral color component corresponding to oblique position 118-2 may correspond to a wavelength corresponding to a different particle of the plurality of particles in channel 102. That is, the different particle may have a fluorescent signal with a second spectral color component that corresponds to a wavelength different from that of particle 101, where the second spectral color component is received at detector 114 at oblique position 118-2.

As another example, the third spectral color component corresponding to oblique position 118-3 may correspond to a wavelength corresponding to a further different particle of the plurality of particles in channel 102. That is, the further different particle may have a fluorescent signal with a third spectral color component that corresponds to a wavelength different from that of particle 101 and the different particle, where the further different particle is received at detector 114 at oblique position 118-3.

Although detector 114 is shown in FIG. 1 as having three oblique positions 118-1, 118-2, 118-3, examples of the disclosure are not so limited. For example, detector 114 may have more than three oblique positions or less than three oblique positions allowing for detection of many spectral components with a spectral resolution.

In some examples, detector 114 may be a complementary metal-oxide semiconductor (CMOS) sensor. As used herein, a CMOS sensor may be a semiconductor chip that stores information. For example, a CMOS sensor may be utilized to determine the wavelength of a fluorescent signal of particle 101.

In some examples, detector 114 may be a charge-coupled device (CCD). As used herein, a CCD may be a device for the movement of electrical charge for use in light detection. For example, a CCD may be utilized to determine the wavelength of a fluorescent signal of particle 101.

Although not shown in FIG. 1 for clarity and so as not to obscure examples of the disclosure, spectral microscope 100 may include a plurality of channels in transparent chip 104. Each of the plurality of channels may include a fluid and each fluid may include a plurality of particles, although embodiments of the disclosure are not so limited. For example, the plurality of channels may include a plurality of particles not suspended in a fluid. The plurality of channels may be parallel channels.

In some examples, each of the plurality of channels may include the same fluid. For example, the fluid, and the plurality of particles in each respective fluid in each of the plurality of channels is the same.

In some examples, each of the plurality of channels may include a different fluid. For example, one channel may include a first type of fluid with a plurality of first particles, and a second channel may include a second type of fluid with a plurality of second particles.

Substrate 110 may include a plurality of planar diffractive lenses. The number of planar diffractive lenses may correspond to the number of channels. For example, spectral microscope 100 may include three channels and three planar diffractive lenses. Each of the plurality of planar diffractive lenses may include an axial focus and an oblique focus Each of the plurality of planar diffractive lenses may include a respective phase profile. That is, each of the plurality of planar diffractive lenses may include an axial phase profile corresponding to the axial focus of the lens and an oblique phase profile corresponding to the oblique focus of the lens.

In some examples, each of the plurality of planar diffractive lenses may include the same phase profile. For example, if each of the plurality of channels includes the same fluid with the same type of particles in each respective fluid to be identified, each of the plurality of planar diffractive lenses may have the same phase profile.

Each of the respective phase profiles of the plurality of planar diffractive lenses may be determined based on a type of particle to be detected. For example, if one channel includes a first type of fluid with a plurality of first particles to be detected, and a second channel includes a second type of fluid with a plurality of second particles to be detected, and the plurality of first particles are different from the plurality of second particles, the first planar diffractive lens corresponding to the channel with the first type of fluid may have a phase profile that is different from the phase profile of the second planar diffractive lens corresponding to the channel with the second type of fluid.

A light source may generate an excitation light to excite a fluorescent signal of the plurality of particles included in each of the fluids of the plurality of channels. For example, a light source (e.g., an LED or laser) may generate an excitation light to excite a fluorescent signal of a plurality of particles of two different fluids in two different channels. As another example, a light source (e.g., an LED or laser) may generate an excitation light to excite a fluorescent signal of a plurality of particles of two fluids in two different channels, where the two fluids are the same fluid. As used herein, an excitation light may be a light generated by the light source at a wavelength that may produce a fluorescent signal of a particular particle.

In some examples, more than one light source may generate an excitation light to excite a fluorescent signal of the plurality of particles included in each of the fluids of the plurality of channels. For example, two light sources (e.g., two LED's or two lasers) may generate excitation lights to excite fluorescent signals of a plurality of particles of two different fluids in two different channels, where each light source corresponds to a respective channel.

In some examples, the two light sources may have different light intensities. For example, a first LED may have a light intensity of 100 mW, while a second LED may have a light intensity of 25 mW.

A plurality of detectors may correspond to the plurality of channels and the plurality of planar diffractive lenses. The plurality of detectors may receive each respective one of the excitation light from each of the respective axial foci for each of the planar diffractive lenses. Further, the plurality of detectors may receive a spectral color component of each of the respective fluorescent signals of the plurality of particles from each of the respective oblique foci of each of the plurality of planar diffractive lenses. That is, each detector may receive an excitation light from each respective axial foci of each respective planar diffractive lens. Further, each detector may receive a spectral color component from each respective oblique foci of each respective planar diffractive lens.

In some examples, a detector may correspond to the plurality of channels and the plurality of diffractive lenses. The detector may receive each one of the excitation light from each of the axial foci for each of the planar diffractive lenses. Further, the detector may receive a spectral color component of each of the respective fluorescent signals of the plurality of particles from each of the respective oblique foci of each of the plurality of planar diffractive lenses. That is, the detector may receive an excitation light from each respective axial foci of each respective planar diffractive lens. Further, the detector may receive a spectral color component from each respective oblique foci of each respective planar diffractive lens.

As described herein, a spectral microscope may include a channel in a transparent chip, where the channel includes a plurality of particles. A light source may excite a fluorescent signal of a particle among the plurality of particles, where the fluorescent signal is propagated through a planar diffractive lens. A detector may receive light generated from the light source from an axial focus of the planar diffractive lens in order to image the particle, and receive a spectral color component from the oblique focus of the planar diffractive lens in order to identify a wavelength of the particle. Examples consistent with the disclosure may reduce the size and cost of spectral microscopes, allowing for use in applications such as point-of-care medical tests and diagnosis. Further, the spectral microscope consistent with the disclosure may be easily adapted and integrated for use with existing microfluidic channel devices, although embodiments of the disclosure are not so limited.

Figure 2:
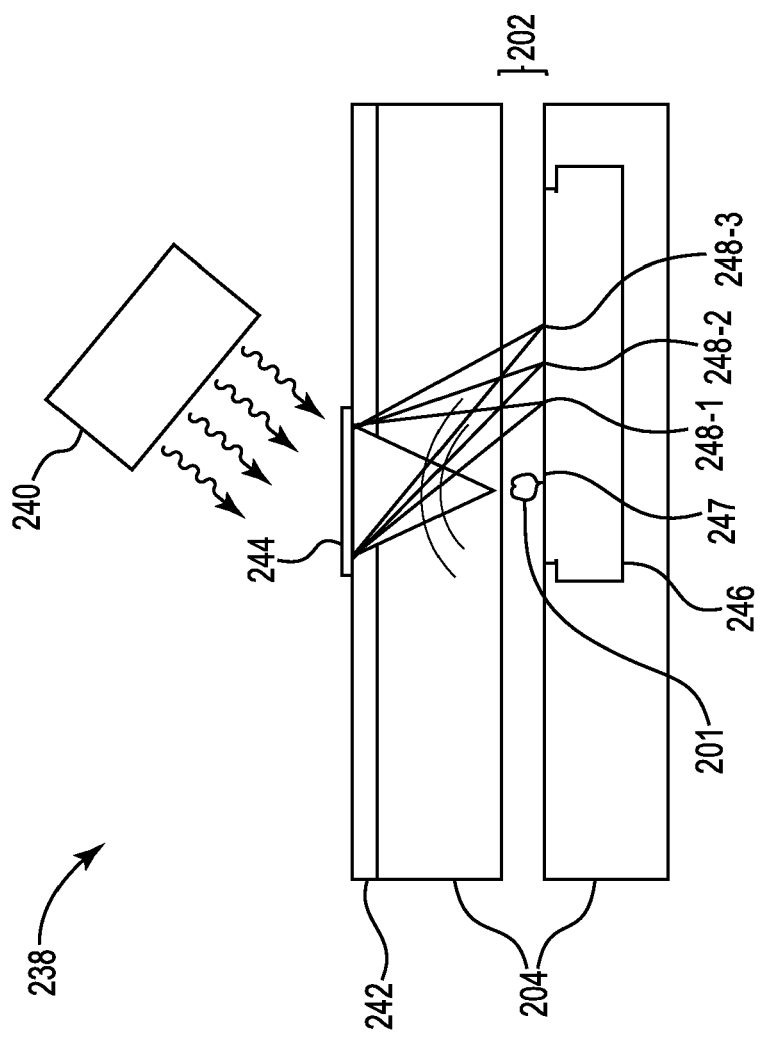
FIG. 2 illustrates a diagram of an example of a spectral microscope consistent with the disclosure.

FIG. 2 illustrates a diagram of an example of a spectral microscope 238 consistent with the disclosure. The spectral microscope 238 may include a transparent chip 204, a channel 202, a particle 201, a substrate 242, a planar reflective lens 244, a light source 240, and a detector 246. Detector 246 may include an axial position 247 and oblique position 248-1, 248-2, 248-3.

Similar to the spectral microscope described in FIG. 1 (e.g., spectral microscope 100), spectral microscope 238 may include a transparent chip 204 that includes a channel 202. Transparent chip 204 may be a transparent material to allow light from a light source (e.g., light source 108) to propagate through transparent chip 204, as will be further described herein. For example, transparent chip 204 may be fused silica. As another example, transparent chip may be fused quartz or glass.

As shown in FIG. 2, spectral microscope 238 may include a substrate 242 with a planar reflective lens 244. Planar reflective lens may be a partially-reflective lens. As used herein, a partially-reflective lens may be a lens that allows light to be partially transmitted and partially reflected. Planar reflective lens 244 may include a phase profile including an axial focus and an oblique focus. Planar reflective lens 244 may be a high numerical aperture reflective lens with two foci (e.g., axial focus and oblique focus). The axial focus of planar reflective lens 244 may be used for focusing the excitation and the oblique focus of planar reflective lens 244 may be used for spectral detection, as will be further described herein.

Similar to the example described in FIG. 1, planar reflective lens 244 may be located on substrate 242. For example, planar reflective lens 244 may be a lens patterned on substrate 242. Planar reflective lens 244 may be patterned on substrate 242 by lithography to create planar reflective lens 244.

Substrate 242 may be a transparent material to allow light from a light source (e.g., light source 240) to propagate through substrate 242. Substrate 242 may be chosen according to the wavelength of operation of light source 240. For example, substrate 242 may be glass, a graded fused silica, quartz, or calcium fluoride, although examples of the disclosure are not so limited.

Similar to the example described in FIG. 1, spectral microscope 238 may include light source 240 to excite a fluorescent signal of particle 201 among the plurality of particles. Particle 201 may include a fluorescent signal and a wavelength corresponding to the fluorescent signal. Light source 240 may be a LED or a laser.

Spectral microscope 238 may include a detector 246. Detector 246 may receive light generated from light source 240 from the axial focus of planar reflective lens 244, and a spectral color component of the fluorescent signal of particle 201 can be reflected from the oblique focus of planar reflective lens 244. As shown in FIG. 2, detector 246 may be part of transparent chip 204 and located adjacent to channel 202.

Detector 246 may receive light generated from light source 240 from the axial focus of planar reflective lens 244 at axial position 247. For example, the axial phase profile of planar reflective lens 244 may cause light from light source 240 to be focused in an axial manner to axial position 247 on the focal plane of detector 246. Light received at axial position 247 of detector 246 may be used to image particle 201.

The fluorescent signal from particle 201 may be received at detector 246 at an oblique position 248-1, 248-2, 248-3. For example, the light generated by light source 240 may propagate through substrate 242, through transparent chip 204, through particle 201, and excite a fluorescent signal that is collected by the axial phase profile of the planar reflective lens 244, where the axial phase profile of the planar diffractive lens directs (e.g., reflects) the light to axial position 247 at detector 246.

Light received at oblique positions 248-1, 248-2, 248-3 of detector 246 may be used to detect the wavelength of the fluorescent signal of particle 201. Detector 246 may determine the wavelength of the fluorescent signal of particle 201 by determining which oblique position 248-1, 248-2, 248-3 the light from light source 240 is received at. Oblique positions 248-1, 248-2, 248-3 of detector 246 may correspond to different spectral color components. For example, oblique position 248-1 may correspond to a first spectral color component, oblique position 248-2 may correspond to a second spectral color component, and oblique position 248-3 may correspond to a third spectral color component.

The spectral color component may be received at detector 246 at oblique position 248-1, 248-2, 248-3 from an oblique phase profile of planar reflective lens 244. For example, the light generated by light source 240 may propagate through substrate 242, excite a fluorescent signal of particle 201, and reflect off transparent chip 204 to the oblique phase profile of planar reflective lens 244. The oblique phase profile of the planar reflective lens 244 directs (e.g., reflects) the spectral color component to a respective oblique position 248-1, 248-2, 248-3 at detector 246.

Figure 3:
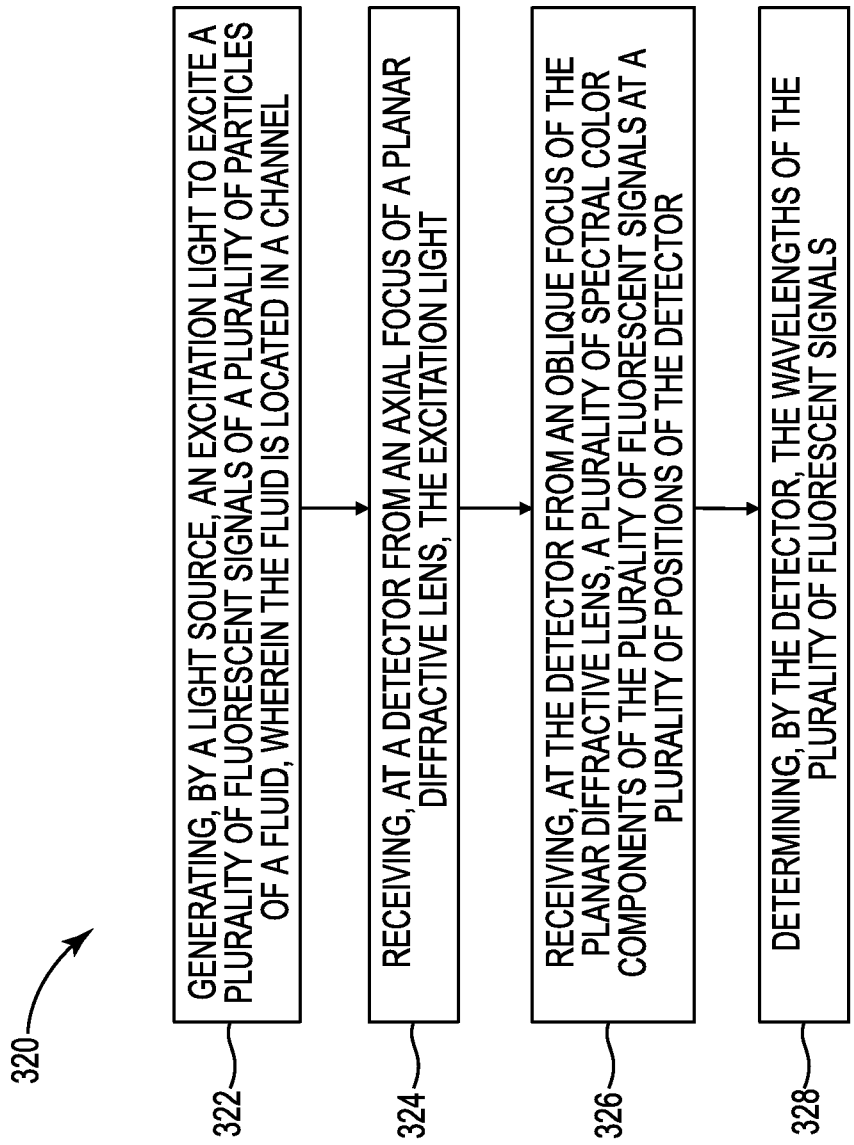
FIG. 3 illustrates a flow chart of an example method of a spectral microscope consistent with the disclosure.

FIG. 3 illustrates a flow chart of an example method 320 of a spectral microscope (e.g., spectral microscope 100, 238 described in connection with FIGS. 1 and 2, respectively) consistent with the disclosure. For example, method 320 may be performed by a detector (e.g., detector 114, 247 described in connection with FIGS. 1 and 2, respectively) to determine wavelengths of a plurality of fluorescent signals.

As illustrated at 322, the method 320 may include generating, by a light source (e.g., light source 108, 240, described in connection with FIGS. 1 and 2, respectively), an excitation light to excite a plurality of fluorescent signals of a plurality of particles of a fluid, wherein the fluid is located in a channel (e.g., channel 102, 202, described in connection with FIGS. 1 and 2, respectively). The excitation light may be generated with enough optical power to generate fluorescent excitation of a fluorescent signal of the plurality of particles that may be detected by the detector.

In some examples, the excitation light may propagate from the light source through a transparent chip (e.g., transparent chip 104, described in connection with FIG. 1) and further through the channel including the fluid with the plurality of particles. The excitation light may illuminate a particle (e.g., particle 101, previously described in connection with FIG. 1) among the plurality of particles of the fluid in the channel. The excitation light may then propagate through the transparent chip (e.g., transparent chip 104, previously described in connection with FIG. 1), and through a planar diffractive lens (e.g., planar diffractive lens 112, previously described in connection with FIG. 1).

In some examples, the excitation light may propagate from the light source through a substrate (e.g., substrate 242, described in connection with FIG. 2) and further through a transparent chip (e.g., transparent chip 204, described in connection with FIG. 2) and further through the channel including the fluid with the plurality of particles. The excitation light may illuminate a particle (e.g., particle 201, described in connection with FIG. 2) among the plurality of particles of the fluid in the channel. The excitation light is again reflected off the planar reflective lens.

As illustrated at 324, the method 320 may include receiving, at the detector from an axial focus of the planar diffractive lens, the excitation light. For example, after propagating through the planar diffractive lens, the excitation light may be received at the detector at an axial position (e.g., axial position 116, 247, described in connection with FIGS. 1 and 2, respectively).

The excitation light may be received at the detector at the axial position from an axial phase profile of the planar diffractive lens or the planar reflective lens. For example, the excitation light may propagate through the axial phase profile of the planar diffractive lens or reflect off the planar reflective lens, where the axial phase profile of the planar diffractive lens or the planar reflective lens directs the excitation light to the axial position at the detector.

The excitation light received from the axial focus of the planar diffractive lens or the planar reflective lens may be used for imaging the particle. For example, imaging the particle may include determining the size and/or shape of the particle. The size and/or shape of the particle may be useful for diagnostic measurements taken using the spectral microscope.

Although imaging the particle is described as determining the size and/or shape of the particle, examples of the disclosure are not so limited. For example, imaging the particle may include determining other physical characteristics of the particle.

As illustrated at 326, the method 320 may include receiving, at the detector from an oblique focus of the planar diffractive lens or the planar reflective lens, a plurality of spectral color components of the plurality of fluorescent signals at a plurality of positions of the detector. For example, after propagating through the planar diffractive lens or reflecting off the planar reflective lens, the spectral color component of a fluorescent signal of a particle among the plurality of particles may be received at the detector at an oblique position (e.g., oblique position 118-1, 118-2, 118-3, 248-1, 248-2, 248-3, described in connection with FIGS. 1 and 2, respectively).

The spectral color component may be received at the detector at an oblique position from an oblique phase profile of the planar diffractive lens or planar reflective lens. For example, the excitation light may propagate through the oblique phase profile of the planar diffractive lens or reflect off of the oblique phase profile of the planar reflective lens after illuminating (e.g., exciting) the fluorescent signal of a particle. The oblique phase profile of the planar diffractive lens or planar reflective lens directs the spectral color component to an oblique position at the detector.

Receiving the plurality of spectral color components at the detector may include receiving different spectral color components of the plurality of spectral color components at different positions on the detector. Different particles may have different fluorescent signals that may correspond to unique spectral color components. For example, a first particle with a first spectral color component may have a different fluorescent signal than a second particle with a second spectral color component. The first spectral color component of the first particle will be received at the detector at a first oblique position, and the second spectral color component of the second particle will be received at the detector at a second oblique position, where the first oblique position at the detector is different from the second oblique position at the detector.

Different positions on the detector may correspond to different wavelengths of the plurality of fluorescent signals. For example, the first spectral color component of the first particle received at a first oblique position may correspond to a wavelength of 635 nanometers (nm). The second spectral color component of the second particle received at a second oblique position may correspond to a wavelength of 645 nm.

Although the first oblique position of the detector and the second oblique position of the detector are described as corresponding to wavelengths of 635 nm and 645 nm, respectively, examples of the disclosure are not so limited. For example, the different positions on the detector may correspond to any other wavelength.

As illustrated at 328, the method 320 may include determining, by the detector, the wavelengths of the plurality of fluorescent signals. The wavelengths of the plurality of fluorescent signals may be determined using the excitation light received from the axial focus of the planar diffractive lens or the planar reflective lens and the respective position at the detector at which each of the plurality of spectral color components are received from the oblique focus of the planar diffractive lens or planar reflective lens.

The wavelength of a fluorescent signal of a particle may be determined by determining the position at which the spectral color component of the fluorescent signal of the particle is received at the detector. For example, if the spectral color component of the particle is received at the oblique position of the detector corresponding to a yellow spectral color component, and the oblique position of the detector corresponding to a yellow spectral color component corresponds to a wavelength of 635 nm, the detector may determine the wavelength of the fluorescent signal of the particle is 635 nm. As another example, if the spectral color component of the particle is received at the oblique position of the detector corresponding to a blue spectral color component, and the oblique position of the detector corresponding to the blue spectral color component corresponds to a wavelength of 645 nm, the detector may determine the wavelength of the fluorescent signal of the particle is 645 nm.

In some examples, the detector may utilize the excitation light received from the axial focus of the planar diffractive lens or planar reflective lens to correct for a lateral shift of the position of the particle. For example, a spectral color from a particle that has a lateral shift with respect to the center of the microfluidic channel may be received at an oblique position at the detector that is not expected. The detector may utilize the excitation light from the axial focus to correct for a shift of the spectral color component.

The wavelengths of the plurality of fluorescent signals of the plurality of particles may be determined as the fluid flows through the channel. For example, the fluid including the plurality of particles may be flowing through the channel while the excitation light from the light source excites the fluorescent signal of the plurality of particles.

The wavelengths of the plurality of fluorescent signals of the plurality of particles may be determined as the detector moves past the transparent chip. For example, the transparent chip can be fixed while the detector and the light source move past the transparent chip such that the excitation light from the light source excites the fluorescent signal of a plurality of particles.

As described herein, a method may include generating an excitation light by a light source to excite a plurality of fluorescent signals of a plurality of particles. A detector may receive the excitation light from an axial focus of a planar diffractive lens or a planar reflective lens, and a plurality of spectral color components of the plurality of fluorescent signals from an oblique focus of the planar diffractive lens or the planar reflective lens. The detector may further determine the wavelengths of the plurality of fluorescent signals based on the excitation light received from the axial focus of the planar diffractive lens or planar reflective lens and the respective position at the detector at which each of the plurality of spectral color components are received from the oblique focus of the planar diffractive lens or planar reflective lens. Utilizing this method may allow for particle imaging and detection using integrated components in a compact spectral microscope, eliminating the need for systems with large optical components with complicated and/or delicate alignment configurations.

Figure 4:
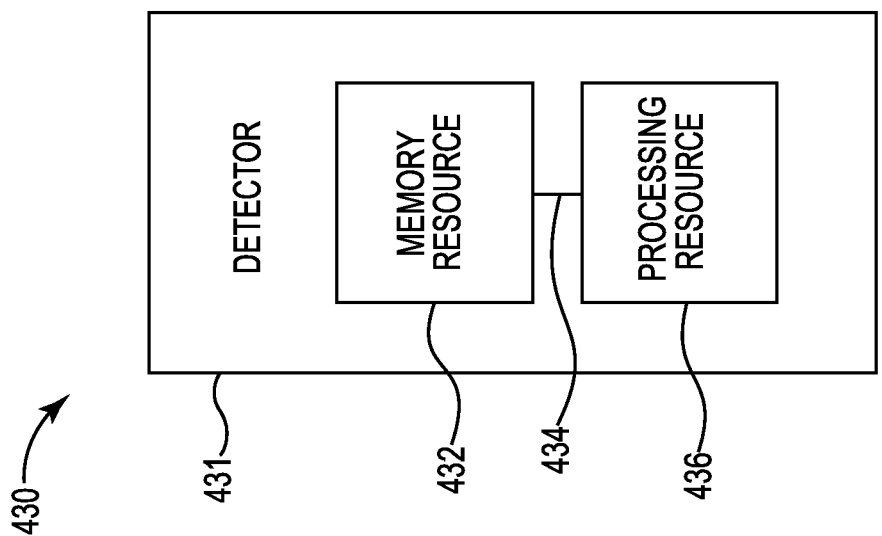
FIG. 4 illustrates a diagram of an example of a detector for a spectral microscope consistent with the disclosure.

FIG. 4 illustrates a diagram of an example of a detector 431 (e.g., detector 114, 247, described in connection with FIGS. 1 and 2, respectively) for a spectral microscope (e.g., spectral microscope 100, 238, described in connection with FIGS. 1 and 2, respectively) consistent with the disclosure. The detector 431 may include a memory resource 432 and a processing resource 436.

Detector 431 may include hardware, machine readable instructions on a non-transitory machine readable medium, or a combination thereof, to perform the elements described in connection with FIGS. 1-3.

The hardware, for example, may include processing resource 436 and/or memory resource 432 (e.g., computer-readable medium (CRM), machine readable medium (MRM), database, etc.). A processing resource 436, as used herein, may include any number of processors capable of executing instructions stored by memory resource 432. Processing resource 436 may be implemented in a single device or distributed across multiple devices. The machine readable instructions (e.g., computer readable instructions (CRI)) may include instructions stored on the memory resource 432 and executable by the processing resource 436 to implement a desired element (e.g., a detector 431 to determine the wavelengths of a plurality of fluorescent signals based on an excitation light received from an axial focus of a planar lens and a respective position at detector 431 at which each of a plurality of spectral color components are received from an oblique focus of the planar lens, etc.).

The memory resource 432 may be in communication with the processing resource 436. The memory resource 432, as used herein, may include any number of memory components capable of storing instructions that may be executed by processing resource 436. Such a memory resource 432 may be non-transitory CRM or MRM. Memory resource 432 may be integrated in a single device or distributed across multiple devices. Further, memory resource 432 may be fully or partially integrated in the same device as processing resource 436, or they may be separate but accessible to those devices and processing resources 436. Thus, it is noted that the detector 431 may be implemented on a participant device, on a server device, on a collection of server devices, and/or a combination of the participant device and the server device.

The memory resource 432 may be in communication with the processing resource 436 via a communication link (e.g., a path) 434. The communication link 434 may be local or remote to the machine (e.g., detector 431) associated with the processing resource 436. Examples of a local communication link 434 may include an electronic bus internal to a machine (e.g., a detector) where the memory resource 432 is one of volatile, non-volatile, fixed, and/or removable storage medium in communication with the processing resource 436 via the electronic bus.

As used herein, "logic" is an alternative or additional processing resource to perform a particular action and/or element described herein. Logic may include hardware. The hardware may include processing resources such as circuitry, which are distinct from machine readable instructions on a machine readable media. Further, as used herein, "a" or "a number of" something may refer to one or more such things. For example, "a number of widgets" may refer to one or more widgets.

The above specification, examples and data provide a description of the method and applications, and use of the system and method of the disclosure. Since many examples may be made without departing from the spirit and scope of the system and method of the disclosure, this specification merely sets forth some of the many possible example configurations and implementations.

What is claimed is:

1. A spectral microscope, comprising:
   a substrate with a planar lens patterned on the substrate, the planar lens including a sinusoidal grating having a single pattern phase profile including an axial focus and an oblique focus;
   a light source to excite a signal of a particle among a plurality of particles; and
   a detector to receive:
      light generated from the light source from the axial focus of the planar lens; and
      a spectral color component of the excited signal of the particle from the oblique focus of the planar lens.

2. The spectral microscope of claim 1, wherein the plurality of particles are located in a fluid.

3. The spectral microscope of claim 1, wherein the spectral color component of the oblique focus corresponds to a wavelength of the excited signal.

4. The spectral microscope of claim 1, wherein the phase profile of the planar lens includes:
   an axial phase profile based on the axial focus of the planar lens; and
   an oblique phase profile based on the oblique focus of the planar lens.

5. The spectral microscope of claim 1, wherein the planar lens is a diffractive lens.

6. The spectral microscope of claim 1, wherein the light source is a light emitting diode.

7. The spectral microscope of claim 1, wherein the light source is a laser.

8. A method, comprising:
   generating, by a light source, an excitation light to excite a plurality of fluorescent signals of a plurality of particles of a fluid, wherein the fluid is located in a channel in a transparent chip;
   directing, by a planar lens patterned on a substrate including a sinusoidal grating having a single pattern phrase profile including an axial focus and an oblique focus, the excitation light;
   receiving, at a detector from the axial focus of the planar lens, the excitation light;
   receiving, at the detector from the oblique focus of the planar lens, a plurality of spectral color components of the plurality of fluorescent signals at a plurality of positions of the detector; and
   determining, by the detector, the wavelengths of the plurality of fluorescent signals based on:
      the excitation light received from the axial focus of the planar lens; and
      the respective position at the detector at which each of the plurality of spectral color components are received from the oblique focus of the planar lens.

9. The method of claim 8, wherein the method further includes receiving different spectral color components of the plurality of spectral color components at different positions on the detector.

10. The method of claim 8, wherein different positions on the detector correspond to different wavelengths of the plurality of fluorescent signals.

11. The method of claim 8, wherein the wavelengths of the plurality of fluorescent signals of the plurality of particles are determined as the fluid flows through the channel.

12. The method of claim 8, wherein the wavelengths of the plurality of fluorescent signals of the plurality of particles are determined as the detector moves past the transparent chip.

13. A spectral microscope, comprising:
   a plurality of channels in a transparent chip, wherein each of the plurality of channels includes a fluid and wherein each of the fluids of the plurality of channels comprise a plurality of particles;
   a substrate with a plurality of planar lenses each patterned on the substrate, wherein each of the plurality of planar lenses includes a sinusoidal grating having a single pattern phrase profile including an axial focus and an oblique focus;

a light source to generate an excitation light to excite a fluorescent signal of the plurality of particles included in each of the fluids of the plurality of channels; and a plurality of detectors to receive each respective one of:
the excitation light from each of the respective axial foci of each of the planar lenses; and
a spectral color component of each of the respective fluorescent signals of the plurality of particles from each of the respective oblique foci of each of the plurality of planar lenses.

14. The spectral microscope of claim 13, wherein each of the plurality of planar lenses includes a respective phase profile.

15. The spectral microscope of claim 14, wherein each of the respective phase profiles of the plurality of planar lenses are determined based on a type of particle to be detected.

16. The spectral microscope of claim 1, wherein the detector is positioned above the substrate.

17. The spectral microscope of claim 1, further comprising a transparent chip having a channel including the plurality of particles.

18. The spectral microscope of claim 17, wherein the detector is positioned in the transparent chip and located adjacent to the channel.

19. The spectral microscope of claim 1, wherein the planar lens is a partially reflective lens.

20. The spectral microscope of claim 19, wherein the partially reflective lens reflects the spectral color component to the detector.

* * * * *